United States Patent
Lorant et al.

(10) Patent No.: US 7,744,858 B2
(45) Date of Patent: Jun. 29, 2010

(54) STABLE COMPOSITION WITH HIGH ELECTROLYTE CONTENT CONTAINING AN AMPHIPHILIC POLYMER

(75) Inventors: Raluca Lorant, Thiais (FR); Paula Lennon, Lyons (FR)

(73) Assignee: L'Oreal, Clichy (FR)

( * ) Notice: Subject to any disclaimer, the term of this patent is extended or adjusted under 35 U.S.C. 154(b) by 0 days.

(21) Appl. No.: 10/181,983

(22) PCT Filed: Jan. 8, 2002

(86) PCT No.: PCT/FR02/00045

§ 371 (c)(1),
(2), (4) Date: Jul. 24, 2002

(87) PCT Pub. No.: WO02/055038

PCT Pub. Date: Jul. 18, 2002

(65) Prior Publication Data

US 2003/0036490 A1 Feb. 20, 2003

(30) Foreign Application Priority Data

Jan. 11, 2001 (FR) .................................. 01 00337

(51) Int. Cl.
| | | |
|---|---|---|
| A61K 8/00 | (2006.01) | |
| A61K 8/18 | (2006.01) | |
| A61K 8/02 | (2006.01) | |
| A61K 9/66 | (2006.01) | |
| A61K 33/14 | (2006.01) | |
| A61Q 5/00 | (2006.01) | |
| A61Q 9/00 | (2006.01) | |
| A01N 59/08 | (2006.01) | |

(52) U.S. Cl. ........................ 424/70.1; 424/401; 424/455; 424/665

(58) Field of Classification Search ................ 424/70.1, 424/400, 401, 455, 665; 514/772, 772.4
See application file for complete search history.

(56) References Cited

U.S. PATENT DOCUMENTS

| | | | |
|---|---|---|---|
| 4,460,732 A | 7/1984 | Buscall et al. | |
| 4,861,499 A | 8/1989 | Neff et al. | |
| 5,089,578 A | 2/1992 | Valint et al. | |
| 5,114,706 A | 5/1992 | Duvel | |
| 5,464,452 A | 11/1995 | Cole et al. | |
| 6,277,388 B1 * | 8/2001 | Chevalier | ................... 424/401 |
| 6,645,476 B1 * | 11/2003 | Morschhauser et al. | .... 424/70.1 |

FOREIGN PATENT DOCUMENTS

| | | |
|---|---|---|
| EP | 0 406 042 | 1/1991 |
| EP | 0 750 899 | 1/1997 |
| EP | 0 815 843 | 1/1998 |
| EP | 0 815 847 | 1/1998 |
| EP | 0 970 682 | 1/2000 |
| EP | 1 055 406 | 11/2000 |
| JP | 08 252447 | 10/1996 |
| WO | 00 31154 | 6/2000 |

OTHER PUBLICATIONS

U.S. Appl. No. 10/181,412, filed Jul. 23, 2002, Lorant, et al.
U.S. Appl. No. 10/181,981, filed Jul. 24, 2002, Guillou, et al.
U.S. Appl. No. 10/166,128, filed Jun. 11, 2002, L'Alloret, et al.
A. Kobayashi et al.: "Solubilization properties of N-substituted amphiphilic acrylamide copolymers" Journal of Applied Polymer Science., vol. 73, No. 12, pp. 2447-2453 Sep. 19, 1999.

* cited by examiner

*Primary Examiner*—Sreeni Padmanabhan
*Assistant Examiner*—Samira Jean-Louis
(74) *Attorney, Agent, or Firm*—Oblon, Spivak, McClelland, Maier & Neustadt, L.L.P.

(57) ABSTRACT

The present invention relates to a composition for topical application, comprising at least one electrolyte and at least one amphiphilic polymer including at least one ethylenically unsaturated monomer containing a sulphonic group, in free form or partially or totally neutralized form and comprising at least one hydrophobic portion.

The invention also relates to the uses of the said composition, especially in cosmetics, to treat and care for human skin, the scalp, mucous membranes, the nails and keratin fibres.

77 Claims, No Drawings

STABLE COMPOSITION WITH HIGH ELECTROLYTE CONTENT CONTAINING AN AMPHIPHILIC POLYMER

The present invention relates to a stable composition for topical application, comprising at least one electrolyte and at least one amphiphilic polymer, and to its use especially for treating and caring for human skin, the scalp, mucous membranes, the nails and keratin fibres (hair or eyelashes).

In the cosmetic, dermatological and pharmaceutical fields, it is known practice to use topical compositions in the form of aqueous gels or of emulsions comprising gelling agents which give these compositions consistency. The majority of the gelling agents conventionally used are carboxyvinyl polymers, which are neutralized with a base.

However, it is found that certain compounds that it is desired to use in these compositions do not allow the use of the abovementioned gelling agents due to incompatibility.

It is known, for example, that electrolytes (mineral and organic salts) are incompatible with neutralized carboxyvinyl polymers because they "break" the emulsion and liquefy it. Thus, compositions containing carboxyvinyl polymers and electrolytes lack consistency, which is the opposite of the result desired by the use of a gelling agent.

Now, it may be desirable to introduce electrolytes into thickened compositions, especially topical compositions, and occasionally even in a relatively large amount, especially when these electrolytes have a beneficial effect on the skin or the hair and are combined with cosmetic and/or dermatological active agents that themselves have beneficial effects on the skin, in particular when the electrolytes are used to reduce the irritation of active agents with an irritant side effect. The gelling agent must be compatible with the electrolytes while at the same time retaining the efficacy of the active agent and of the electrolytes. In addition, the composition must be clear and stable.

One solution consists in using, instead of carboxyvinyl polymers, gelling agents of polysaccharide type, such as guar gum or xanthan gum or cellulose derivatives. The use of natural gums such as xanthan gum or carrageenans has a tendency to make the products runny and heavy on application. Moreover, compositions based on cellulose derivatives, such as described in document EP-A-654 270, do not have a smooth texture, but instead have a lumpy appearance that looks relatively unpleasant. In addition, these compositions leave the skin sticky and "as if wet" after application, since these compositions do not penetrate sufficiently into the skin. This combination of factors makes them unacceptable for use in cosmetics and/or dermatology.

Combining these cellulose derivatives with another thickener such as a silicate, as described, for example, in document WO-A-93/8230, gives compositions in which the same drawbacks as mentioned above (lumpy appearance) remain.

Moreover, crosslinked anionic copolymers comprising 2-acrylamido-2-methylpropanesulphonic groups, such as the product sold by the company SEPPIC under the name Sepigel 305 (consisting of units derived from the reaction between (i) acrylamide, (ii) 2-acrylamido-2-methylpropanesulphonic acid and (iii) at least one compound containing olefinic polyunsaturation) also do not make it possible to obtain compositions containing a large amount of electrolytes while retaining a sufficient viscosity.

In addition, although the use of 2-acrylamido-2-methylpropanesulphonic acid (AMPS) homopolymers, such as the product sold by the company Clariant under the name Hostacerin AMPS, makes it possible to obtain the gelation of aqueous media while at the same time retaining good cosmetic properties, when compared with other available gelling agents, the addition of electrolytes causes thinning of the gels obtained, that is to say that they lose their viscosity and become more fluid.

There is thus still a need for gel compositions containing electrolytes, which do not have the drawbacks of the prior art.

The Applicant has found, unexpectedly, an amphiphilic polymer that makes it possible to stabilize compositions containing electrolytes, without causing the thinning of the said compositions.

Thus, one subject of the present invention is a composition for topical application, including an aqueous phase comprising at least one electrolyte and at least one amphiphilic polymer including at least one ethylenically unsaturated monomer containing a sulphonic group, in free form or partially or totally neutralized form and comprising at least one hydrophobic portion.

Since the composition of the invention is intended for topical application, it comprises a physiologically acceptable medium. In the present patent application, the expression "physiologically acceptable medium" means a medium that is compatible with all keratin materials, such as the skin, including the scalp, the nails, the mucous membranes, the eyes and the hair, or any other area of body skin.

The composition obtained shows excellent stability and retains a satisfactory viscosity in the presence of electrolyte, even at a high proportion of electrolytes, without unacceptable thinning as is the case for the gelling agents of the prior art.

Thus, a subject of the present invention is also the use of an amphiphilic polymer including at least one ethylenically unsaturated monomer containing a sulphonic group, in free form or partially or totally neutralized form and comprising at least one hydrophobic portion, to obtain a stable cosmetic or dermatological composition containing at least one electrolyte.

The expression "stable composition" means a composition whose viscosity remains virtually constant after addition of electrolyte, or whose viscosity varies within an acceptable limit (for example less than 30% reduction in the viscosity).

In the present invention, the term "electrolyte" means all salts and polyions, especially polyanions, which may be used in a topical composition.

The composition obtained is clear and has the desired viscosity, that is to say a viscosity of greater than a few poises, for example from 5 to 80 poises (0.5 to 8 Pa·s), preferably from 10 to 50 poises (1 to 5 Pa·s) and better still from 15 to 30 poises (1.5 to 3 Pa·s), the said viscosity being measured at room temperature (about 25° C.) with a Rheomat 180 using a No. 2, 3, 4 or 5 spindle depending on the viscosity range, at 200 $s^{-1}$.

Amphiphilic Polymers According to the Invention

The polymers in accordance with the invention are amphiphilic polymers comprising at least one ethylenically unsaturated monomer containing a sulphonic group, in free form or partially or totally neutralized form and comprising at least one hydrophobic portion.

The expression "amphiphilic polymer" means any polymer comprising both a hydrophilic portion and a hydrophobic portion and especially a fatty chain.

The hydrophobic portion present in the polymers of the invention preferably contains from 6 to 50 carbon atoms, more preferably from 6 to 22 carbon atoms, even more preferably from 6 to 18 carbon atoms and more particularly from 12 to 18 carbon atoms.

Preferably, the polymers in accordance with the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The amphiphilic polymers in accordance with the invention generally have a number-average molecular weight ranging from 1000 to 20 000 000 g/mol, preferably ranging from 20 000 to 5 000 000 and even more preferably from 100 000 to 1 500 000 g/mol.

The amphiphilic polymers according to the invention may or may not be crosslinked. Crosslinked amphiphilic polymers are preferably chosen.

When they are crosslinked, the crosslinking agents may be chosen from compounds containing olefinic polyunsaturation commonly used for the crosslinking of polymers obtained by free-radical polymerization.

Mention may be made, for example, of divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylol propane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl(meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to 10 mol % and more particularly from 0.2 mol % to 2 mol % relative to the polymer.

The ethylenically unsaturated monomers containing a sulphonic group are chosen especially from vinylsulphonic acid, styrenesulphonic acid, (meth)acrylamido($C_1$-$C_{22}$)alkylsulphonic acids, N—($C_1$-$C_{22}$)alkyl(meth)acrylamido($C_1$-$C_{22}$) alkylsulphonic acids, for instance undecylacrylamidomethanesulphonic acid, and also partially or totally neutralized forms thereof.

(Meth)acrylamido($C_1$-$C_{22}$)alkylsulphonic acids such as, for example, acrylamidomethanesulphonic acid, acrylamidoethanesulphonic acid, acrylamidopropane-sulphonic acid, 2-acrylamido-2-methylpropanesulphonic acid, methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid or 2-acrylamido-2,6-dimethyl-3-heptanesulphonic acid, and also partially or totally neutralized forms thereof, will more preferably be used.

2-Acrylamido-2-methylpropanesulphonic acid (AMPS), and also its partially or totally neutralized forms, will more particularly be used.

The amphiphilic polymers in accordance with the invention may be chosen especially from random amphiphilic polymers of AMPS modified by reaction with a $C_6$-$C_{22}$ n-monoalkylamine or di-n-alkylamine, and such as those described in patent application WO-A-00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of the invention are chosen from amphiphilic copolymers of AMPS and of at least one ethylenically unsaturated hydrophobic monomer comprising at least one hydrophobic portion containing from 6 to 50 carbon atoms, more preferably from 6 to 22 carbon atoms, even more preferably from 6 to 18 carbon atoms and more particularly 12 to 18 carbon atoms.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, U.S. Pat. No. 5,089,578 and in the following publications from Yotaro Morishima:

"Self-assembling amphiphilic polyelectrolytes and their nanostructures—Chinese Journal of Polymer Science Vol. 18, No. 40, (2000), 323-336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704";

"Solution properties of micelle networks formed by nonionic moieties covalently bound to a polyelectrolyte: salt effects on rheological behavior—Langmuir, 2000, Vol. 16, No. 12, 5324-5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The ethylenically unsaturated hydrophobic monomers of these particular copolymers are preferably chosen from the acrylates or acrylamides of formula (I) below:

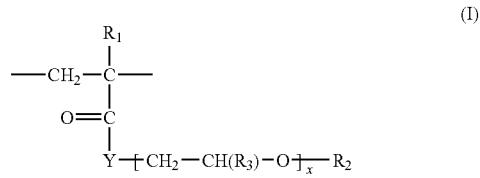

(I)

in which $R_1$ and $R_3$, which may be identical or different, denote a hydrogen atom or a linear or branched $C_1$-$C_6$ alkyl radical (preferably methyl); Y denotes O or NH; $R_2$ denotes a hydrophobic hydrocarbon-based radical containing at least from 6 to 50 carbon atoms, more preferably from 6 to 22 carbon atoms, even more preferably from 6 to 18 carbon atoms and more particularly from 12 to 18 carbon atoms; x denotes a number of moles of alkylene oxide and ranges from 0 to 100.

The radical $R_2$ is preferably chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkylperfluoro radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, the ones that are more particularly preferred are linear alkyl radicals and more particularly the n-dodecyl or n-hexadecyl radical.

According to one particularly preferred form of the invention, the monomer of formula (I) comprises at least one alkylene oxide unit (x≧1) and preferably a polyoxyalkylenated chain. The polyoxyalkylenated chain preferably consists of ethylene oxide units and/or of propylene oxide units and even more particularly consists of ethylene oxide units. The number of oxyalkylenated units (or number of moles of alkylene oxide) generally ranges from 3 to 100, more preferably from 3 to 50 and even more preferably from 7 to 25.

Among these polymers, mention may be made of:
crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl (meth)acrylate units relative to the polymer, such as those described in patent application EP-A-750 899;
terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in U.S. Pat. No. 5,089,578.

Mention may also be made of copolymers of totally neutralized AMPS and of dodecyl or n-hexadecyl methacrylate, and also crosslinked and non-crosslinked copolymers of AMPS and of n-dodecylmethacrylamide, such as those described in the Morishima articles mentioned above.

Mention will be made more particularly of the copolymers consisting of 2-acrylamido-2-methylpropanesulphonic acid (AMPS) units of formula (II) below:

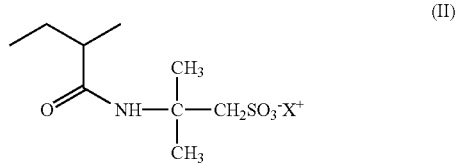

(II)

in which $X^+$ is a proton, an alkali metal cation, an alkaline-earth metal cation or the ammonium ion, and of units of formula (III) below:

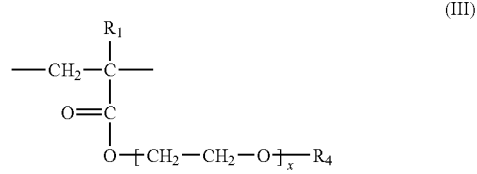

(III)

in which x denotes an integer ranging from 3 to 100, preferably from 5 to 80 and more preferably from 7 to 25; $R_1$ has the same meaning as that given above in formula (I) and $R_4$ denotes a linear or branched $C_6$-$C_{22}$ and more preferably $C_{10}$-$C_{22}$ alkyl.

The polymers that are particularly preferred are those for which x=25, $R_1$ denotes methyl and $R_4$ represents n-dodecyl; they are described in the Morishima articles mentioned above. Other preferred polymers are those for which x=25, $R_1$ denotes methyl and $R_4$ represents n-hexadecyl or n-octadecyl.

The polymers for which $X^+$ denotes sodium or ammonium are more particularly preferred.

The preferred amphiphilic polymers in accordance with the invention may be obtained according to the standard free-radical polymerization processes in the presence of one or more initiators such as, for example, azobisisobutyronitrile (AIBN), azobisdimethylvaleronitrile, 2,2-azobis[2-amidinopropane]hydrochloride (ABAH=2,2-AzoBis[2-Amidinopropane]Hydrochloride), organic peroxides such as dilauryl peroxide, benzoyl peroxide, tert-butyl hydroperoxide, etc., mineral peroxide compounds such as potassium persulphate or ammonium persulphate, or $H_2O_2$ optionally in the presence of reducing agents.

The amphiphilic polymers are obtained especially by free-radical polymerization in tert-butanol medium in which they precipitate. Using precipitation polymerization in tert-butanol, it is possible to obtain a size distribution of the polymer particles that is particularly favourable for its uses.

The size distribution of the polymer particles may be determined, for example, by laser diffraction or image analysis. An advantageous distribution for this type of polymer, determined by image analysis, is as follows: 60.2% less than 423 microns, 52.0% less than 212 microns, 26.6% less than 106 microns, 2.6% less than 45 microns and 26.6% greater than 850 microns.

The reaction may be performed at a temperature of between 0 and 150° C., preferably between 10 and 100° C., either at atmospheric pressure or under reduced pressure. It may also be performed under inert atmosphere, and preferably under nitrogen.

According to this process 2-acrylamido-2-methylpropane-sulphonic acid (AMPS) or a sodium or ammonium salt thereof was especially polymerized with a (meth)acrylic acid ester and
a $C_{10}$-$C_{18}$ alcohol oxyethylenated with 8 mol of ethylene oxide (Genapol® C-080 from the company Hoechst/Clariant),
a $C_{11}$ oxo alcohol oxyethylenated with 8 mol of ethylene oxide (Genapol® UD-080 from the company Hoechst/Clariant),
a $C_{11}$ oxo alcohol oxyethylenated with 7 mol of ethylene oxide (Genapol® UD-070 from the company Hoechst/Clariant),
a $C_{12}$-$C_{14}$ alcohol oxyethylenated with 7 mol of ethylene oxide (Genapol® LA-070 from the company Hoechst/Clariant),
a $C_{12}$-$C_{14}$ alcohol oxyethylenated with 9 mol of ethylene oxide (Genapol® LA-090 from the company Hoechst/Clariant),
a $C_{12}$-$C_{14}$ alcohol oxyethylenated with 11 mol of ethylene oxide (Genapol® LA-110 from the company Hoechst/Clariant),
a $C_{16}$-$C_{18}$ alcohol oxyethylenated with 8 mol of ethylene oxide (Genapol® T-080 from the company Hoechst/Clariant),
a $C_{16}$-$C_{18}$ alcohol oxyethylenated with 15 mol of ethylene oxide (Genapol® T-150 from the company Hoechst/Clariant),
a $C_{16}$-$C_{18}$ alcohol oxyethylenated with 11 mol of ethylene oxide (Genapol® T-110 from the company Hoechst/Clariant),
a $C_{16}$-$C_{18}$ alcohol oxyethylenated with 20 mol of ethylene oxide (Genapol® T-200 from the company Hoechst/Clariant),
a $C_{16}$-$C_{18}$ alcohol oxyethylenated with 25 mol of ethylene oxide (Genapol® T-250 from the company Hoechst/Clariant),
a $C_{18}$-$C_{22}$ alcohol oxyethylenated with 25 mol of ethylene oxide and/or a $C_{16}$-$C_{18}$ iso alcohol oxyethylenated with 25 mol of ethylene oxide.

The molar % concentration of the units of formula (II) and of the units of formula (III) in the polymers according to the invention will vary as a function of the desired cosmetic use and of the desired rheological properties of the formulation. It may range between 0.1 mol % and 99.9 mol %.

Preferably, for the most hydrophobic polymers, the molar proportion of units of formula (I) or (III) ranges from 50.1% to 99.9%, more particularly from 70% to 95% and even more particularly from 80% to 90%.

Preferably, for the sparingly hydrophobic polymers, the molar proportion of units of formula (I) or (III) ranges from 0.1% to 50%, more particularly from 5% to 25% and even more particularly from 10% to 20%.

The monomer distribution in the polymers of the invention may be, for example, alternating, block (including multiblock) or random.

According to the invention, it is preferable for the polymers to contain heat-sensitive pendant chains and for the aqueous solution thereof to have a viscosity that, beyond a certain threshold temperature, increases or remains virtually constant as the temperature increases.

Even more particularly, the preferred polymers are those whose aqueous solution has a viscosity that is low below a first threshold temperature and that, above this first threshold temperature, increases to a maximum as the temperature increases, and that, above a second threshold temperature, decreases again as the temperature increases. From this perspective, it is preferable for the viscosity of the polymer solutions below the first threshold temperature to be from 5% to 50%, in particular from 10% to 30% of the maximum viscosity at the second threshold temperature.

These polymers preferably lead in water to a phenomenon of demixing by heating, reflected by curves showing, as a function of the temperature and the concentration, a minimum known as the LCST (Lower Critical Solution Temperature).

The viscosities (measured at 25° C. using a Brookfield viscometer, needle No. 7) of the aqueous 1% solutions preferably range from 20 000 mPa·s to 100 000 mPa·s and more particularly from 60 000 mPa·s to 70 000 mPa·s.

The amphiphilic polymers in accordance with the invention are present in the compositions in concentrations ranging from 0.01% to 30% by weight of active material, more preferably from 0.1% to 10% of active material, even more preferably from 0.1% to 5% by weight of active material and even more particularly from 0.2% to 2% by weight of active material relative to the total weight of the composition.

The electrolyte may be present in the composition of the invention in an amount ranging, for example, from 0.01% to 20% by weight of active material, preferably from 0.01% to 10% and better still from 0.05% to 5% by weight relative to the total weight of the composition. This amount of electrolyte varies especially according to the electrolyte used and the desired aim of the final composition.

As electrolytes that may be used in the composition according to the invention, mention may be made especially of mono-, di- or trivalent metal salts, and more particularly alkaline-earth metal salts and in particular barium, calcium and strontium salts, alkali metal salts, and for example sodium and potassium salts, and also magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminium, silicon and selenium salts, and mixtures thereof.

The ions constituting these salts may be chosen, for example, from carbonates, bicarbonates, sulphates, phosphates, sulphonates, glycerophosphates, borates, bromides, chlorides, nitrates, acetates, hydroxides and persulphates, and also ions of α-hydroxy acids (citrates, tartrates, lactates or malates) or of fruit acids, ions of β-hydroxy acids (salicylates, 2-hydroxyalkanoates, n-alkylsalicylates and n-alkanoyl-salicylates), or ions of amino acids (aspartate, arginate, glycocholate or fumarate).

It is also possible to use a mixture of these salts, including natural mixtures or mixtures whose composition is close to that of a natural mixture, and in particular an aqueous mixture comprising from 30% to 35% magnesium chloride, from 20% to 28% potassium chloride, from 3% to 10% sodium chloride, from 0.2% to 1% calcium chloride, from 0.1% to 0.6% magnesium bromide and from 0.1% to 0.5% insolubles, the said mixture being referred to herein as "Dead Sea bath salts mixture" since it corresponds to the main salts contained in the Dead Sea.

It is also possible to use salts that are in the form of a solution or a water containing them, and especially in the form of a thermal spring water or mineral water. In general, a mineral water is fit for consumption, which is not always the case for a thermal spring water. Each of these waters contains, inter alia, dissolved minerals and trace elements.

The thermal spring water or mineral water used may be chosen, for example, from eau de Vittel, waters from the Vichy basin, eau d'Uriage, eau de la Roche Posay, eau de la Bourboule, eau d'Enghien-les-bains, eau de Saint-Gervais-les bains, eau de Néris-les-bains, eau d'Allevard-les-bains, eau de Digne, eau des Maizières, eau de Neyrac-les-bains, eau de Lons le Saunier, Eaux Bonnes, eau de Rochefort, eau de Saint Christau, eau des Fumades, eau d'Avène and eau de Tercis-les-bains.

The electrolytes of the composition of the invention may also be chosen from the salts of active agents, for example salts derived from vitamins, for instance vitamin C (ascorbic acid) or vitamin A (retinol), or the salts of acidic active agents, for instance the salts of acidic screening agents). Examples of salts derived from vitamins that may be mentioned include the ascorbyl phosphate of an alkali metal, alkaline-earth metal or transition metal, for instance magnesium, sodium, potassium, calcium or zinc; the retinyl phosphate of an alkali metal or alkaline-earth metal, for instance magnesium or potassium. Examples of salts derived from screening agents that may be mentioned include benzene-1,4-[di(3-methylidene-10-camphorsulphonic) acid] salts, the sodium sulphonate of 2-hydroxy-4-methoxy-5-benzophenone acid (or benzophenone-5) and the disodium salt of 2,2'-dihydroxy-4, 4'-dimethoxy-5,5'-disulphobenzophenone (or benzophenone-9).

The physiologically acceptable medium for the composition of the invention comprises water. The amount of water may range from 5% to 99.98% by weight and preferably from 30% to 95% by weight relative to the total weight of the composition. This medium may contain, besides water, one or more solvents chosen from lower alcohols containing from 1 to 8 carbon atoms, such as ethanol; polyols such as glycerol; glycols, for instance butylene glycol, isoprene glycol, propylene glycol, or polyethylene glycols such as PEG-8; sorbitol; sugars such as glucose, fructose, maltose, lactose or sucrose; and mixtures thereof. The amount of solvent(s) in the composition of the invention may range from 0.2% to 30% by weight and preferably from 1% to 20% by weight relative to the total weight of the composition.

The composition of the invention preferably has a pH that is compatible with the skin, that is to say preferably ranging from 3 to 8 and better still from 5 to 7.

The composition of the invention may also contain one or more additives that are common in cosmetics and/or dermatology, such as surfactants, active agents, fillers, pigments, nacres, preserving agents, gelling agents, plasticizers, antioxidants, fragrances, odour absorbers, antifoams, sequestering agents (EDTA), acidic or basic pH regulators or buffers, fatty substances, for instance oils or waxes, and mixtures thereof, provided that the additive does not adversely affect the desired properties for the composition of the invention.

The amounts of these various additives are those conventionally used in the fields under consideration, and for example from 0.01% to 20% relative to the total weight of the composition.

The composition according to the invention may be in any pharmacological form that is suitable for topical application, and especially in the form of an aqueous or aqueous-alcoholic gel, an emulsion, especially an O/W emulsion, or an aqueous dispersion based on ionic and/or nonionic lipid vesicles, optionally containing a dispersed oil. It may, for example, constitute a serum, a cream or a milk.

The composition according to the invention may also contain at least one oily phase.

When the composition of the invention is an emulsion, the proportion of the fatty phase (or oily phase) may range from 5% to 80% by weight and preferably from 10% to 50% by weight relative to the total weight of the composition, and the proportion of aqueous phase may range from 20% to 95% and preferably from 50% to 90% by weight relative to the total weight of the composition. The oils, emulsifiers and co-emulsifiers used in the composition in emulsion form are chosen from those conventionally used in the field under consideration. The oily phase contains one or more oils, that is to say organic substances that are liquid at room temperature (20 to 25° C.) and at atmospheric pressure (760 mm Hg).

As oils which can be used in the composition of the invention, mention may be made for example of:

hydrocarbon-based oils of animal origin, such as perhydrosqualene;

hydrocarbon-based plant-origin oils such as liquid triglycerides of fatty acids containing from 4 to 10 carbon atoms, such as heptanoic or octanoic acid triglycerides or alternatively, for example, sunflower oil, corn oil, soya bean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil or karite butter;

synthetic esters and ethers in particular of fatty acids, such as the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate;

linear or branched hydrocarbons of mineral or synthetic origin, such as volatile or non-volatile liquid paraffins and derivatives thereof, petroleum jelly, polydecenes or hydrogenated polyisobutene such as parleam;

fatty alcohols containing from 8 to 26 carbon atoms, such as cetyl alcohol, stearyl alcohol, and the mixture thereof (cetylstearyl alcohol), octyldodecanol, 2-butyloctanol, 2-hexyldecanol, 2-undecylpentadecanol oleyl alcohol, or linoleyl alcohol;

partially hydrocarbon-based and/or silicone-based fluoro oils such as those described in document JP-A-2 295 912;

silicone oils such as volatile or non-volatile polymethylsiloxanes (PDMSs) containing a linear or cyclic silicone-based chain, which are liquid or pasty at room temperature, in particular cyclopolydimethylsiloxanes (cyclomethicones) such as cyclohexasiloxane; polydimethylsiloxanes comprising alkyl, alkoxy or phenyl groups, pendant or at the end of a silicone-based chain, these groups containing from 2 to 24 carbon atoms; phenylsilicones such as phenyl trimethicones, phenyl dimethicones, phenyltrimethyl-siloxydiphenylsiloxanes, diphenyl dimethicones, diphenylmethyldiphenyltrisiloxanes, 2-phenylethyl trimethylsiloxysilicates and polymethylphenylsiloxanes;

mixtures thereof.

"Hydrocarbon-based oil" is understood to mean, in the list of oils mentioned above, any oil containing a majority of carbon and hydrogen atoms and optionally ester, ether, fluoro, carboxylic acid and/or alcohol groups.

The other fatty substances which may be present in the oily phase are, for example, fatty acids containing from 8 to 30 carbon atoms, for instance stearic acid, lauric acid or palmitic acid; waxes, for instance lanolin, beeswax, carnauba wax, candelilla wax, paraffin wax, lignite wax or microcrystalline waxes, ceresine or ozokerite, synthetic waxes, for instance polyethylene waxes and Fischer-Tropsch waxes; gums such as silicone gums (dimethiconol); silicone resins such as trifluoromethyl-C1-4-alkyldimethicone and trifluoropropyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art in order to prepare a composition having the desired properties, for example of consistency or of texture.

According to one particular embodiment of the invention, when the composition is an O/W emulsion, it may be prepared without addition of emulsifiers, by virtue of the amphiphilic nature of the polymer. Thus, due to the absence of an emulsifying surfactant, this emulsion has the advantage of not being irritant to skin that is particularly sensitive and/or reactive, and it can constitute a hypoallergenic product. The polymer used according to the invention thus makes it possible to prepare emulsifier-free oil-in-water emulsions.

A subject of the invention is thus also an emulsion comprising an oily phase dispersed in an aqueous phase, characterized in that it is free of emulsifier and in that it contains at least one amphiphilic polymer including at least one ethylenically unsaturated monomer containing a sulphonic group, in free form or partially or totally neutralized form and comprising at least one hydrophobic portion.

The composition according to the invention may be used in many cosmetic or dermatological applications in which the presence of salts is useful; it may especially be used for treating, caring for and/or making up facial and/or body skin, mucous membranes (lips), the scalp and/or keratin fibres (hair or eyelashes), and also for treating sensitive skin and/or a sensitive scalp. For example, it may be used for moisturizing the skin and for giving the skin a radiant complexion such as an anti-ageing skincare product.

Thus, the compositions of the invention may be used as care products and/or hygiene products such as protective, treatment or care creams for the face, for the hands or for the body, protective or care body milks, lotions, milks, gels or mousses to care for the skin and mucous membranes or for cleansing, removing make-up from or scrubbing skin. They may also constitute make-up products for keratin fibres, the skin, the lips and/or the nails, such as a foundation, a face powder, an eyeshadow, a lipstick, a mascara or an eyeliner.

The compositions of the invention may also be used as antisun products for protecting the skin against UV rays.

Thus, one subject of the present invention is the cosmetic use of the cosmetic composition as defined above, to treat, care for and/or make up the facial and/or body skin, mucous membranes (lips), the scalp and/or keratin fibres.

A subject of the present invention is also the use of the composition as defined above for the manufacture of a composition intended for treating sensitive skin and/or a sensitive scalp. For further details regarding sensitive skin, reference may be made to document EP-A-680 749.

Another subject of the invention is a cosmetic process for treating human keratin materials such as the skin, including the scalp, the hair, the eyelashes, the eyebrows, the nails or the mucous membranes, especially the lips, characterized in that a cosmetic composition as defined above is applied to the keratin materials according to the usual technique for using this composition. For example: application of creams, gels, sera, lotions or milks to the skin, the scalp and/or the mucous membranes. The type of treatment depends on the electrolyte(s) present in the composition.

PREPARATION EXAMPLES

Preparation of Ethoxylated (Meth)Acrylic Esters

These may especially be obtained by the action of glycidyl (meth)acrylate or (meth)acrylic acid or an alkyl(meth)acrylate or a (meth)acryloyl halide on an ethoxylated fatty alcohol. Non-limiting examples which may be mentioned include the following preparations:

a) starting with glycidyl methacrylate and Genapol T-250;
b) starting with (meth)acrylic acid and Genapol UD-070;
c) starting with methyl(meth)acrylate and Genapol LA-090;
d) starting with (meth)acryloyl chloride and Genapol UD-070.

a) 500 g of Genapol T-250 and 75 g of glycidyl methacrylate are placed in a one-liter three-necked reactor equipped with a stirrer, a thermometer and a reflux condenser. The reaction mixture is heated at a temperature of 100° C. for 2 hours and the excess glycidyl methacrylate is removed by distillation under reduced pressure. The monomer obtained may be used for the polymerization without further purification.

b) 500 g of Genapol UD-070, 100 g of (meth)acrylic acid and p-toluenesulphonic acid as catalyst are placed in a one-liter three-necked reactor equipped with a stirrer, a thermometer and a reflux condenser. The reaction mixture is refluxed for 2 hours and the excess acid and the water formed during the reaction are separated out by distillation under reduced pressure. The monomer obtained may be used for the polymerization without further purification.

c) 500 g of Genapol LA-090, 100 g of methyl (meth) acrylate and 20 g of titanium tetraisopropoxide are placed in a one-liter three-necked reactor equipped with a stirrer, a thermometer and a reflux condenser. The reaction mixture is refluxed for 2 hours and, after separation by distilling off the alcohol formed, the remaining ester is distilled under reduced pressure. The monomer obtained may be used for the polymerization without further purification.

d) 500 g of Genapol UD-070, 110 g of (meth)acryloyl chloride and 50 g of sodium carbonate are placed in a one-liter three-necked reactor equipped with a stirrer, a thermometer and a reflux condenser. The reaction mixture is refluxed for 2 hours and the excess acid chloride is separated out by distillation under reduced pressure. The monomer obtained may be used for the polymerization without further purification.

Polymerization According to the Precipitation Method in Tert-Butanol 500 ml of tert-butanol and the calculated amount of AMPS are placed in a 2-liter reactor equipped with a reflux condenser, a gas inlet, a thermometer and a stirrer. The mixture is neutralized by introducing $NH_3$, and the monomer prepared above is added to the reaction mixture. The reaction mixture is made inert by passing nitrogen or argon through, and, when the internal temperature has reached 60° C., the initiator (AIBN) is introduced to initiate the polymerization. After a few minutes, the polymer thus prepared precipitates. The mixture is maintained at reflux for 2 hours, and the polymer is separated from the solvent by vacuum filtration and then dried under reduced pressure.

The following polymers were prepared in the manner described above:
(starting with the following reagents in amounts expressed in grams)

| | | | | |
|---|---|---|---|---|
| Genapol T-250 methacrylate | 10 | 20 | 30 | 97 |
| AMPS neutralized with $NH_3$ | 90 | 80 | 90 | 3 |
| Methylenebisacrylamide (crosslinking agent) | | | 1.5 | |
| Allyl methacrylate (crosslinking agent) | | 1.7 | | |
| TMPTA (crosslinking agent) | 1.8 | | | 1.8 |
| Azobisisobutyronitrile (initiator) | | | 1 | |
| Dilauryl peroxide (initiator) | 1 | 1 | | 1 |
| tert-Butanol | 300 | 300 | 300 | 300 |

The following were prepared in the same manner:

a copolymer crosslinked with allyl methacrylate, consisting of 80% by weight of AMPS units neutralized with $NH_3$, and of 20% by weight of Genapol T-250 methacrylate units [units of formula (III) in which $R_1=CH_3$, $R_4=C_{16}-C_{18}$ and x=25];

a copolymer crosslinked with allyl methacrylate, consisting of 90% by weight of AMPS units neutralized with $NH_3$, and of 10% by weight of Genapol LA-070 methacrylate units [units of formula (III) in which $R_1=H$, $R_4=C_{12}-C_{14}$ and x=7].

Examples of Compositions

The examples which follow illustrate the invention without being limiting in nature. The amounts are indicated as percentages by weight, except where otherwise mentioned.

Example 1

Aqueous Gel for Skin Care (Moisturization and Radiance of the Complexion)

| | |
|---|---|
| Crosslinked copolymer of AMPS (*) | 2% |
| Magnesium ascorbyl phosphate | 2% |
| Demineralized water | qs 100% |

(*) Copolymer crosslinked with allyl methacrylate, consisting of 90% by weight of AMPS units neutralized with $NH_3$, and of 10% by weight of Genapol LA-070 methacrylate units [units of formula (III) in which $R_1 = H$, $R_4 = C_{12}-C_{14}$ and x = 7].

The gel obtained has a viscosity of about 20 poises (2.0 Pa·s), the viscosity being measured at about 25° C. with a Rheomat 180 machine using a No. 3 spindle, at $200\ s^{-1}$. The gel has a very smooth appearance. The viscosity of the same gel without magnesium ascorbyl phosphate is about 26 poises, (2.6 Pa·s).

Comparative Examples

Example 1 was repeated, replacing the amphiphilic polymer used according to the invention, with polymers of the prior art: Hostacerin AMPS (AMPS homopolymer sold by the company Hoechst-Clariant) and Sepigel 305 (crosslinked anionic copolymer that is substantially water-soluble, consisting of units derived from the reaction between (i) acrylamide, (ii) 2-acrylamido-2-methylpropanesulphonic acid, and (iii) at least one compound containing olefinic polyunsaturation, sold by the company Seppic). The viscosity of the gel is measured with and without addition of 0.1% by weight of magnesium ascorbyl phosphate (MAP) (viscosity measured at about 25° C. with a Rheomat 180 machine using a No. 3 spindle, at 200 s$^{-1}$).

As shown in the table below, a large variation in viscosity is observed with these polymers of the prior art when an electrolyte is added thereto.

| Polymers | Example of the invention | | Comparative Example 1 | | Comparative Example 1a | |
|---|---|---|---|---|---|---|
| | without MAP | with 1% MAP | without MAP | with 1% MAP | without MAP | with 1% MAP |
| Amphiphilic polymer of the invention | 2% | 2% | | | | |
| Hostacerin AMPS | | | 2% | 2% | | |
| Sepigel 305 | | | | | 2% | 2% |
| Viscosity | 26.6 poises (2.66 Pa.s) | 20.5 poises (2.05 Pa.s) | 42.4 poises (4.24 Pa.s) | 19.9 poises (1.99 Pa.s) | 24.5 poises (2.45 Pa.s) | 0.62 poises (0.062 Pa.s) |
| Variation in viscosity | −23% | | −53% | | −97% | |

The variation in the viscosity by further addition of electrolyte is much smaller with the amphiphilic polymer used in the composition of the invention than with the gelling polymers of the prior art.

Example 2

Facial Care Cream (O/W Emulsion)

| Oily phase: | |
|---|---|
| Mineral oil | 5% |
| Cyclohexadimethylsiloxane | 5% |
| Preserving agent | qs % |

| Aqueous phase: | |
|---|---|
| Magnesium ascorbyl phosphate | 1% |
| Crosslinked copolymer of AMPS (*) | 2% |
| Preserving agent | 0.2% |
| Demineralized water | qs 100% |

(*) Copolymer crosslinked with allyl methacrylate, consisting of 90% by weight of AMPS units neutralized with NH$_3$, and of 10% by weight of Genapol LA-070 methacrylate units [units of formula (III) in which R$_1$ = H, R$_4$ = C$_{12}$-C$_{14}$ and x = 7].

Procedure: The constituents of the aqueous phase are mixed together with stirring until homogeneous, and the prehomogenized oily phase is introduced into this aqueous phase with stirring.

The cream obtained is a stable, homogeneous white cream that is soft on application and is capable of treating facial skin, and in particular of improving the radiance of the complexion.

Comparative Example 2

Example 2 was repeated, replacing the amphiphilic polymer used according to the invention with Sepigel 305. The emulsion obtained is very fluid and demixes immediately (separation of the aqueous phase and the oily phase with release of oil at the surface).

Example 3

Facial Care Cream (O/W Emulsion)

| Oily phase: | |
|---|---|
| Mineral oil | 5% |
| Cyclohexadimethylsiloxane | 5% |
| Preserving agent | qs % |

| Aqueous phase: | |
|---|---|
| Magnesium sulphate | 0.5% |
| Crosslinked copolymer of AMPS (*) | 3% |
| Preserving agent | 0.2% |
| Demineralized water | qs 100% |

(*) Copolymer crosslinked with allyl methacrylate, consisting of 80% by weight of AMPS units neutralized with $NH_3$, and of 20% by weight of Genapol T-250 methacrylate units [units of formula (III) in which $R_1 = CH_3$, $R_4 = C_{16}$-$C_{18}$ and $x = 25$].

Procedure: The copolymer is dispersed in water (it is made to swell) and the magnesium sulphate predissolved in a small amount of water is added to this gel. The mixture is stirred until homogeneous and the prehomogenized oily phase is introduced into this aqueous phase with stirring.

The cream obtained is a stable, homogeneous white cream that is soft on application and is capable of treating facial skin.

Example 4

Foundation

| Phase A: | |
|---|---|
| Uncoated pigments | 6% |
| Phenyltrimethicone | 8% |

| Phase B: | |
|---|---|
| Crosslinked copolymer of AMPS(*) | 2% |

| Phase C: | |
|---|---|
| Magnesium ascorbyl phosphate | 1% |
| Preserving agents | 0.5% |
| Water | qs 100% |

(*) Copolymer crosslinked with allyl methacrylate, consisting of 80% by weight of AMPS units neutralized with $NH_3$, and of 20% by weight of Genapol T-250 methacrylate units [units of formula (III) in which $R_1 = CH_3$, $R_4 = C_{16}$-$C_{18}$ and $x = 25$].

This composition was prepared in the following manner: phase A is prepared in a first stage. Phase B is then dispersed in phase C (water). Phase A is then dispersed in (B+C).

The composition thus obtained is stable over time.

Example 5

Facial Care Cream Containing Dead Sea Salts

| Oily phase: | |
|---|---|
| Mineral oil | 5% |
| Cyclohexadimethylsiloxane | 5% |
| Preserving agent | qs % |

| Aqueous phase: | |
|---|---|
| Mixture of Dead Sea salts | 0.3% |
| Crosslinked copolymer of AMPS (*) | 2% |
| Preserving agent | 0.2% |
| Demineralized water | qs 100% |

(*) Copolymer crosslinked with allyl methacrylate, consisting of 90% by weight of AMPS units neutralized with $NH_3$, and of 10% by weight of Genapol LA-070 methacrylate units [units of formula (III) in which $R_1 = H$, $R_4 = C_{12}$-$C_{14}$ and $x = 7$].

The amount of Dead Sea salts is indicated as active material.

Procedure: The copolymer is dispersed in water (it is made to swell) and the mixture of Dead Sea salts is then added. The resulting mixture is stirred until homogeneous and the prehomogenized oily phase is introduced to this aqueous phase with stirring.

A fine emulsion which constitutes a thick, shiny cream is obtained.

The invention claimed is:

1. A composition comprising an aqueous phase, said aqueous phase comprising at least one electrolyte and at least one crosslinked amphiphilic polymer present in a viscosity stabilizing effective amount, said polymer comprising polymerized units of at least one ethylenically unsaturated monomer comprising a sulphonic group in a free form, a partially neutralized form or a totally neutralized form, and at least one hydrophobic portion, wherein the at least one electrolyte is selected from the group consisting of an alkaline-earth metal salt, a lithium salt, a zinc salt, a manganese salt, an iron salt, a copper salt, a selenium salt, and a mixture thereof, wherein the electrolyte comprises ions chosen from the group consisting of carbonate, bicarbonate, sulphate, phosphate, sulphonate, glycerophosphate, borate, bromide, chloride, nitrate, acetate, hydroxide, persulphate, ions of α-hydroxy acids, ions of fruit acids, ions of β-hydroxy acids, ions of amino acids, and mixtures thereof, and wherein the amount of electrolyte is from 0.01% to 20% by weight relative to the total weight of the composition.

2. The composition according to claim 1, wherein the hydrophobic portion of the amphiphilic polymer comprises from 6 to 50 carbon atoms.

3. The composition according to claim 2, wherein the hydrophobic portion of the amphiphilic polymer comprises from 6 to 22 carbon atoms.

4. The composition according to claim 3, wherein the hydrophobic portion of the amphiphilic polymer comprises from 6 to 18 carbon atoms.

5. The composition according to claim 4, wherein the hydrophobic portion of the amphiphilic polymer comprises from 12 to 18 carbon atoms.

6. The composition according to claim 1, wherein the amphiphilic polymer is partially or totally neutralized with a mineral or organic base.

7. The composition according to claim 1, wherein the amphiphilic polymer has a number-average molecular weight of from 1000 to 20 000 000 g/mol.

8. The composition according to claim 7, wherein the number-average molecular weight is from 20 000 to 5 000 000 g/mol.

9. The composition according to claim 8, wherein the number-average molecular weight is from 100 000 to 1 500 000 g/mol.

10. The composition according to claim 1, wherein an aqueous solution comprising 1% by weight of the polymer has, at a temperature of 25° C., a viscosity, measured using a Brookfield viscometer with a No. 7 needle, of from 20 000 mPa s to 100 000 mPa s.

11. The composition according to claim 1, wherein the amphiphilic polymer is prepared by free-radical precipitation polymerization in tert-butanol.

12. The composition according to claim 1, wherein a crosslinking agent comprises olefinic polyunsaturation.

13. The composition according to claim 12, wherein the crosslinking agent is one or more crosslinking agents selected from the group consisting of methylenebisacrylamide, allyl methacrylate and trimethylolpropane triacrylate (TMPTA).

14. The composition according to claim 1, wherein a degree of crosslinking is from 0.01 mol % to 10 mol % relative to the polymer.

15. The composition according to claim 1, wherein the ethylenically unsaturated monomer comprising a sulphonic group is chosen from the group consisting of vinylsulphonic acid, styrenesulphonic acid, (meth)acrylamido($C_1$-$C_{22}$) alkyl-sulphonic acids, N—($C_1$-$C_{22}$)alkyl(meth)acrylamido-($C_1$-$C_{22}$)alkylsulphonic acids, partially neutralized forms thereof and totally neutralized forms thereof.

16. The composition according to claim 15, wherein the ethylenically unsaturated monomer comprising a sulphonic group is at least one member selected from the group consisting of acrylamidomethanesulphonic acid, acrylamidoethanesulphonic acid, acrylamidopropane-sulphonic acid, 2-acrylamido-2-methylpropanesulphonic acid, methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid, 2-acrylamido-2,6-dimethyl-3-heptanesulphonic acid, partially neutralized forms thereof and totally neutralized forms thereof.

17. The composition according to claim 15, wherein the ethylenically unsaturated monomer comprising a sulphonic group is 2-acrylamido-2-methylpropane-sulphonic acid (AMPS), a partially neutralized form thereof or a totally neutralized form thereof.

18. The composition according to claim 17, wherein the amphiphilic polymer is chosen from the group consisting of random polymers of AMPS modified by reaction with an n-mono($C_6$-$C_{22}$)alkylamine and random polymers of AMPS modified by reaction with a di-n-($C_6$-$C_{22}$)alkylamine.

19. The composition according to claim 17, wherein the amphiphilic polymer of AMPS comprises polymerized units of at least one ethylenically unsaturated monomer not comprising a fatty chain.

20. The composition according to claim 19, wherein the ethylenically unsaturated monomer not comprising a fatty chain is chosen from the group consisting of (meth)acrylic acids, β-substituted alkyl derivatives of (meth)acrylic acid, esters of (meth)acrylic acid obtained with monoalcohols, esters of (meth)acrylic acid obtained with mono-alkylene glycols, esters of (meth)acrylic acid obtained with polyalkylene glycols, esters of β-substituted alkyl derivatives of (meth)acrylic acid obtained with monoalcohols, esters of β-substituted alkyl derivatives of (meth)acrylic acid obtained with mono-alkylene glycols, esters of β-substituted alkyl derivatives of (meth)acrylic acid obtained with polyalkylene glycols, (meth)acrylamides, vinylpyrrolidone, maleic anhydride, itaconic acid, maleic acid, and mixtures thereof.

21. The composition according to claim 1, wherein the amphiphilic polymer is an amphiphilic copolymer of AMPS and polymerized units of at least one ethylenically unsaturated hydrophobic monomer wherein said copolymer comprises at least one hydrophobic portion comprising from 6 to 50 carbon atoms.

22. The composition according to claim 21, wherein the hydrophobic portion comprises from 6 to 22 carbon atoms.

23. The composition according to claim 22, wherein the hydrophobic portion comprises from 6 to 18 carbon atoms.

24. The composition according to claims 23, wherein the hydrophobic portion comprises from 12 to 18 carbon atoms.

25. The composition according to claim 21, wherein the ethylenically unsaturated hydrophobic monomer is an acrylate or acrylamide of formula (I):

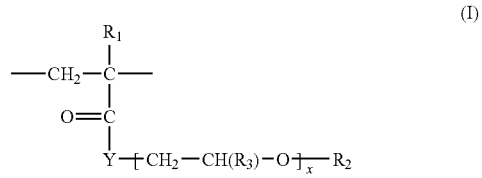

in which $R_1$ and $R_3$, which may be identical or different, are a hydrogen atom or a linear or branched $C_1$-$C_6$ alkyl radical; Y is O or NH; $R_2$ is a hydrophobic hydrocarbon-based radical comprising at least from 6 to 50 carbon atoms; and x is from 0 to 100.

26. The composition according to claim 25, wherein the hydrophobic radical $R_2$ is chosen from the group consisting of linear $C_6$-$C_{18}$ alkyl radicals, branched $C_6$-$C_{18}$ alkyl radicals, cyclic $C_6$-$C_{18}$ alkyl radicals, $C_6$-$C_{18}$ alkylperfluoro radicals, cholesteryl radical, a cholesterol ester, and aromatic polycyclic groups.

27. The composition according to claim 25, wherein the monomer of formula (I) comprises at least one alkylene oxide unit and x>1.

28. The composition according to claim 25, wherein the monomer of formula (I) comprises at least one polyoxyalkylenated chain.

29. The composition according to claim 28, wherein the polyoxyalkylenated chain comprises ethylene oxide units and/or propylene oxide units.

30. The composition according to claim 29, wherein the polyoxyalkylenated chain consists of ethylene oxide units.

31. The composition according to claim 25, wherein the number of moles of alkylene oxide is from 3 to 100.

32. The composition according to claim 31, wherein the number of moles of alkylene oxide is from 3 to 50.

33. The composition according to claim 32, wherein the number of moles of alkylene oxide is from 7 to 25.

34. The composition according to claim 33, wherein the amphiphilic polymer of AMPS is at least one member selected from the group consisting of crosslinked copolymers comprising from 15% to 60% by weight of AMPS units and from 40% to 85% by weight of ($C_8$-$C_{16}$)alkyl(meth)acrylamide units, non-crosslinked copolymers comprising from 15% to 60% by weight of AMPS units and from 40% to 85% by weight of ($C_8$-$C_{16}$)alkyl(meth)acrylamide units, neutralized copolymers comprising from 15% to 60% by weight of AMPS units and from 40% to 85% by weight of ($C_8$-$C_{16}$) alkyl(meth)acrylamide units, non-neutralized copolymers comprising from 15% to 60% by weight of AMPS units and from 40% to 85% by weight of ($C_8$-$C_{16}$)alkyl(meth)acrylamide units, crosslinked copolymers comprising from 15% to 60% by weight of AMPS units and from 40% to 85% by weight of ($C_8$-$C_{16}$)alkyl(meth)acrylate units, non-crosslinked copolymers comprising from 15% to 60% by weight of AMPS units and from 40% to 85% by weight of $(C_8-C_{16})$alkyl (meth)acrylate units, neutralized copolymers comprising from 15% to 60% by weight of AMPS units and from 40% to 85% by weight of $(C_8-C_{16})$alkyl(meth)acrylate units, non-neutralized copolymers comprising from 15% to 60% by weight of AMPS units and from 40% to 85% by weight of $(C_8-C_{16})$alkyl(meth)acrylate units and terpolymers comprising from 10 mol % to 90 mol % of acrylamide units, from 0.1 mol % to 10 mol % of AMPS units and from 5 mol % to 80 mol % of n-$(C_6-C_{18})$alkylacrylamide units relative to the polymer.

35. The composition according to claim 21, wherein the amphiphilic polymer of AMPS is at least one member selected from the group consisting of non-crosslinked copolymers of partially neutralized AMPS, non-crosslinked copolymers of totally neutralized AMPS, non-crosslinked copolymers of n-dodecyl methacrylate, non-crosslinked copolymers of n-hexadecyl methacrylate, crosslinked copolymers of partially neutralized AMPS, crosslinked totally neutralized AMPS, crosslinked copolymers of n-dodecylmethacrylamide and non-crosslinked copolymers of n-dodecylmethacrylamide.

36. The composition according to claim 21, wherein the amphiphilic polymer of AMPS is a copolymer comprising polymerized units of 2-acrylamido-2-methylpropanesulphonic acid (AMPS) of formula (II):

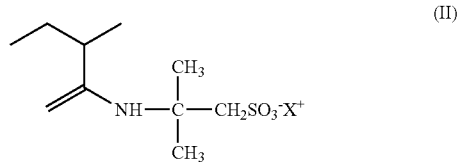

(II)

in which $X^+$ is a proton, an alkali metal cation, an alkaline-earth metal cation or an ammonium ion, and units of formula (III):

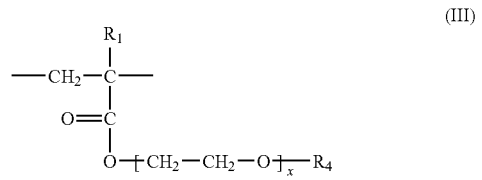

(III)

in which x is an integer of from 3 to 100; $R_1$ is a hydrogen atom or a linear or branched $C_1-C_6$ alkyl radical; and $R_4$ is a linear or branched $C_6-C_{22}$ alkyl.

37. The composition according to claim 36, wherein x=25, $R_1$ is methyl and $R_4$ is n-dodecyl, n-hexadecyl or n-octadecyl.

38. The composition according to claim 25, wherein the % molar proportion of units of formula (I) or of units of formula (III) in the polymer is from 50.1% to 99.9%.

39. The composition according to claim 25, wherein the % molar proportion of units of formula (I) or of units of formula (III) in the polymer is from 0.1% to 50%.

40. The composition according to claim 1, wherein the amount of amphiphilic polymer is from 0.01% to 50% by weight relative to the total weight of the composition.

41. The composition according to claim 1, wherein the electrolyte comprises ions chosen from the group consisting of carbonate, bicarbonate, sulphate, phosphate, sulphonate, glycerophosphate, borate, bromide, chloride, nitrate, acetate, hydroxide, persulphate, ions of α-hydroxy acids, ions of fruit acids, ions of β-hydroxy acids and ions of amino acids.

42. The composition according to claim 1, wherein the electrolyte is a salt of an acidic active agent or a mixture of said salts.

43. The composition according to claim 1, wherein the physiologically acceptable medium comprises water and at least one organic solvent selected from the group consisting of lower alcohols comprising from 1 to 8 carbon atoms, polyols, glycols, sorbitol, sugars, and mixtures thereof.

44. The composition according to claim 1, further comprising at least one oily phase.

45. A care product, a hygiene product, a make-up product or an antisun product comprising the composition according to claim 1.

46. An emulsion comprising an oily phase dispersed in an aqueous phase, wherein said emulsion is free of emulsifier and said emulsion comprises at least one amphiphilic polymer, said polymer comprising polymerized units of at least one ethylenically unsaturated monomer comprising a sulphonic group in a free form, a partially neutralized form or a totally neutralized form and at least one hydrophobic portion, wherein the emulsion further comprises at least one electrolyte selected from the group consisting of an alkaline-earth metal salt, a lithium salt, a zinc salt, a manganese salt, an iron salt, a copper salt, a selenium salt, and a mixture thereof, wherein the electrolyte comprises ions chosen from the group consisting of carbonate, bicarbonate, sulphate, phosphate, sulphonate, glycerophosphate, borate, bromide, chloride, nitrate, acetate, hydroxide, persulphate, ions of α-hydroxy acids, ions of fruit acids, ions of β-hydroxy acids, ions of amino acids, in an amount ranging from 0.01% to 20% by weight relative to the total weight of the composition.

47. The emulsion according to claim 46, comprising a composition comprising an aqueous phase, said aqueous phase comprising at least one electrolyte and at least one amphiphilic polymer, said polymer comprising polymerized units of at least one ethylenically unsaturated monomer comprising a sulphonic group in a free form, a partially neutralized form or a totally neutralized form, and at least one hydrophobic portion.

48. The composition according to claim 14, wherein the degree of crosslinking is from 0.2 mol % to 2 mol % relative to the polymer.

49. The composition according to claim 25, wherein $R_3$ and $R_4$ are methyl.

50. The composition according to claim 25, wherein $R_2$ is a hydrophobic hydrocarbon-based radical comprising at least from 6 to 22 carbon atoms.

51. The composition according to claim 25, wherein $R_2$ is a hydrophobic hydrocarbon-based radical comprising from at least 6 to 18 carbon atoms.

52. The composition according to claim 25, wherein $R_2$ is a hydrophobic hydrocarbon-based radical comprising at least from 12 to 18 carbon atoms.

53. The composition according to claim 36, wherein x is from 5 to 80.

54. The composition according to claim 36, wherein x is from 7 to 25.

55. The composition according to claim 40, wherein the amount of the amphiphilic polymer is from 0.1% to 10% by weight relative to the total weight of the composition.

56. The composition according to claim 40, wherein the amount of the amphiphilic polymer is from 0.1% to 5% by weight relative to the total weight of the composition.

57. The composition according to claim 1, wherein the amount of the electrolyte is from 0.01% to 10% by weight relative to the total weight of the composition.

58. A process for cosmetically treating the skin, said process comprising
applying the composition according to claim 1 to the facial skin, body skin, mucous membranes, the scalp or keratin fibers.

59. A method for cosmetically treating the skin, said method comprising
applying the emulsion according to claim 46 to the facial skin, body skin, mucous membranes, scalp and/or keratin fibers.

60. A method for manufacturing a composition for treating sensitive skin and/or a sensitive scalp, said method comprising
mixing the composition according to claim 1 with a composition intended to treat the skin and/or the scalp.

61. A method for producing a composition for treating sensitive skin and/or a sensitive scalp, said method comprising
mixing the emulsion according to claim 46 with a composition for treating the skin and/or the scalp.

62. A process for cosmetically treating keratin materials, said process comprising
applying the composition according to claim 1 to keratin materials.

63. A process for cosmetically treating keratin materials, said process comprising
applying the emulsion of claim 46 to keratin materials.

64. A process for preparing a stable cosmetic or dermatological composition comprising at least one electrolyte, said process comprising
mixing a crosslinked amphiphilic polymer in an amount sufficient to stabilize the viscosity of the composition, comprising polymerized units of at least one ethylenically unsaturated monomer comprising a sulphonic group in a free form, a partially neutralized form or a totally neutralized form, and at least one hydrophobic portion, with a cosmetic or dermatological composition comprising at least one electrolyte selected from the group consisting of an alkaline-earth metal salt, a lithium salt, a zinc salt, a manganese salt, an iron salt, a copper salt, a selenium salt, and a mixture thereof, wherein the electrolyte comprises ions chosen from the group consisting of carbonate, bicarbonate, sulphate, phosphate, sulphonate, glycerophosphate, borate, bromide, chloride, nitrate, acetate, hydroxide, persulphate, ions of α-hydroxy acids, ions of fruit acids, ions of β-hydroxy acids, ions of amino acids, wherein the amount of electrolyte is from 0.01% to 20% by weight relative to the total weight of the composition.

65. The composition according to claim 1, wherein the at least one amphiphilic polymer is present in an amount sufficient to thicken the aqueous phase and sufficient to stabilize the thickened composition in the presence of the at least one electrolyte.

66. The composition according to claim 1, wherein the amount of the electrolyte is from 0.3% to 10% by weight relative to the total weight of the composition.

67. The composition according to claim 1, wherein the amount of the electrolyte is from 0.5% to 10% by weight relative to the total weight of the composition.

68. The composition according to claim 1, wherein the amount of electrolyte is from 0.3% to 20% by weight relative to the total weight of the composition.

69. The composition according to claim 1, wherein the amount of electrolyte is from 0.5% to 20% by weight relative to the total weight of the composition.

70. The composition according to claim 1, wherein the electrolyte is an alkaline-earth metal salt.

71. The composition according to claim 70, wherein the electrolyte is an alkaline-earth metal sulfate.

72. The composition according to claim 46, wherein the electrolyte comprises at least one alkaline-earth metal.

73. The composition according to claim 46, wherein the ethylenically unsaturated monomer comprising a sulphonic group is chosen from the group consisting of vinylsulphonic acid, styrenesulphonic acid, (meth)acrylamido($C_1$-$C_{22}$) alkyl-sulphonic acids, N—($C_1$-$C_{22}$)alkyl(meth)acrylamido-($C_1$-$C_{22}$)alkylsulphonic acids, partially neutralized forms thereof and totally neutralized forms thereof.

74. The composition according to claim 73, wherein the ethylenically unsaturated monomer comprising a sulphonic group is at least one member selected from the group consisting of acrylamidomethanesulphonic acid, acrylamidoethanesulphonic acid, acrylamidopropane-sulphonic acid, 2-acrylamido-2-methylpropanesulphonic acid, methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid, 2-acrylamido-2,6-dimethyl-3-heptanesulphonic acid, partially neutralized forms thereof and totally neutralized forms thereof.

75. The composition according to claim 73, wherein the ethylenically unsaturated monomer comprising a sulphonic group is 2-acrylamido-2-methylpropane-sulphonic acid (AMPS), a partially neutralized form thereof or a totally neutralized form thereof.

76. The composition according to claim 72, wherein the electrolyte is at least one electrolyte selected from the group consisting of magnesium chloride, calcium chloride, magnesium bromide, mixtures of Dead Sea salts, and mixtures thereof.

77. The composition according to claim 72, wherein the electrolyte is at least one of thermal spring water and a mineral water.

* * * * *

UNITED STATES PATENT AND TRADEMARK OFFICE
CERTIFICATE OF CORRECTION

PATENT NO. : 7,744,858 B2
APPLICATION NO. : 10/181983
DATED : June 29, 2010
INVENTOR(S) : Raluca Lorant et al.

It is certified that error appears in the above-identified patent and that said Letters Patent is hereby corrected as shown below:

Column 19, line 57, delete "or of units of formula (III)";

line 60, delete "or of units of formula (III)".

Column 20, line 32, insert --and-- after "hydroxy acids,".

Column 21, line 51, insert --and-- after "hydroxy acids,".

Column 22, line 20, change "composition" to --emulsion--;

line 22, change "composition" to --emulsion--;

line 29, change "composition" to --emulsion--;

line 41, change "composition" to --emulsion--.

Signed and Sealed this

Twenty-first Day of September, 2010

David J. Kappos
*Director of the United States Patent and Trademark Office*